United States Patent
El Ali et al.

(10) Patent No.: US 9,546,191 B1
(45) Date of Patent: Jan. 17, 2017

(54) PALLADIUM(II) COMPLEX FOR CATALYZING SONOGASHIRA COUPLING REACTIONS AND A METHOD THEREOF

(71) Applicant: KING FAHD UNIVERSITY OF PETROLEUM AND MINERALS, Dhahran (SA)

(72) Inventors: Bassam M. El Ali, Dhahran (SA); Mansur Bala Ibrahim, Dhahran (SA); Rami K. Suleiman, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/081,308

(22) Filed: Mar. 25, 2016

(51) Int. Cl.
| | | |
|---|---|---|
| C07F 15/00 | (2006.01) | |
| C07C 45/68 | (2006.01) | |
| C07C 17/26 | (2006.01) | |
| C07C 253/30 | (2006.01) | |
| C07F 7/08 | (2006.01) | |
| C07F 7/18 | (2006.01) | |
| C07C 29/32 | (2006.01) | |
| C07C 209/68 | (2006.01) | |
| C07B 37/00 | (2006.01) | |
| B01J 31/18 | (2006.01) | |
| C07C 2/86 | (2006.01) | |

(52) U.S. Cl.
CPC .......... *C07F 15/0066* (2013.01); *B01J 31/182* (2013.01); *C07B 37/00* (2013.01); *C07C 2/861* (2013.01); *C07C 17/26* (2013.01); *C07C 29/32* (2013.01); *C07C 45/68* (2013.01); *C07C 209/68* (2013.01); *C07C 253/30* (2013.01); *C07F 7/083* (2013.01); *C07F 7/1892* (2013.01); *B01J 2231/4266* (2013.01); *B01J 2531/824* (2013.01); *C07C 2531/22* (2013.01)

(58) Field of Classification Search
CPC ................................................ C07F 15/0066
See application file for complete search history.

(56) References Cited

U.S. PATENT DOCUMENTS

| 7,642,391 B1 | 1/2010 | Urgaonkar et al. |
| 2006/0058178 A1 | 3/2006 | Kempe et al. |

OTHER PUBLICATIONS

El Hatimi et al. "Chiral bis(oxazoline) ligands. Synthesis of mono- and bi-metallic complexes of nickel and palladium" Journal of the Chemical Society, Dalton Transactions, 1998, pp. 4229-4236.*
Ibrahim et al. "Effective palladium(II)-bis(oxazoline) catalysts: synthesis, crystal structure, and catalytic coupling reactions" Journal of Coordination Chemistry, 2015, vol. 68, pp. 432-448.*
Karami, K., et al., "Copper-Free Sonogashira Cross-Coupling Reactions Catalyzed by an Efficient Dimeric C,N-Palladacycle in DMF/H2O", Turkish Journal of Chemistry, vol. 39, pp. 1199-1207, (2015).
Mery, D., et al., "A Very Efficient, Copper-Free Palladium Catalyst for the Sonogashira Reaction with Aryl Halides", Chemical Communications, pp. 1934-1935, (2003).
Nguyen, P., et al., "Synthesis of Symmetric and Unsymmetric 1,4-bis(p-R-Phenylethynyl) Benzenes via Palladium/Copper Catalyzed Cross-Coupling and Comments on the Coupling of Aryl Halides with Terminal Alkynes ", Inorganica Chimica Acta, vol. 220, pp. 289-296, (1994).
Lin, B.N., et al., "Sonogashira Reaction of Aryl and Heteroaryl Halides with Terminal Alkynes Catalyzed by a Highly Efficient and Recyclable Nanosized MCM-41 Anchored Palladium Bipyridyl Complex", Molecules, vol. 15, pp. 9157-9173, (2010).
Ibrahim, M.B., et al., "Effective Palladium(II)-bis(Oxazoline) Catalysts: Synthesis, Crystal Structure, and Catalytic Coupling Reactions", Journal of Coordination Chemistry, vol. 68, No. 3, pp. 432-448, (2015).
Ibrahim, M.B., et al., "A Highly Active Palladium(II)—bis(Oxazoline) Catalyst for Suzuki—Miyaura, Mizoroki—Heck and Sonogashira Coupling Reactions in Aqueous Dimethylformamide", Applied Organometallic Chemistry, vol. 29, pp. 400-407, (2015).
Liang, B., et al., "Copper-Free Sonogashira Coupling Reaction with PdCl2 in Water under Aerobic Conditions", Journal of Organic Chemistry, vol. 70, pp. 391-393, (2005).
Li, J.H., et al., "Efficient and Copper-Free Sonogashira Cross-Coupling Reaction Catalyzed by Pd(OAc)2/Pyrimidines Catalytic System", European Journal of Organic Chemistry, pp. 4256-4259, (2005).
Sarkar, S.M., et al., "Highly Active Thiol-Functionalized SBA-15 Supported Palladium Catalyst for Sonogashira and Suzuki—Miyaura Cross-Coupling Reactions", Royal Society of Chemistry Advances, vol. 5, pp. 1295-1300, (2015).
Liu, C.. et al., "Palladium-Catalyzed Phosphine-, Copper-Free and Aerobic Sonogashira Coupling in Aqueous Media", Arkivoc, vol. 11, pp. 60-68, (2011).
Bakherad, M., et al., "Solvent-Free Heck and Copper-Free Sonogashira Cross-Coupling Reactions Catalyzed by a Polystyrene-Anchored Pd(II) Phenyldithiocarbazate Complex", Tetrahedron Letters, vol. 53, pp. 5773-5776, (2012).
Ibrahim, M.B., et al., "Synthesis of Functionalized Alkynes via Palladium-Catalyzed Sonogashira Reactions", Tetrahedron Letters, vol. 57, pp. 554-558, (2016).

* cited by examiner

*Primary Examiner* — Joseph Kosack
(74) *Attorney, Agent, or Firm* — Oblon, McClelland, Maier & Neustadt, L.L.P.

(57) ABSTRACT

A palladium(II) complex which catalyzes the Sonogashira coupling reaction efficiently under aerobic condition and a method of employing the palladium(II) complex to synthesize internal alkynes. The palladium(II) complex is an effective catalyst for the coupling reactions of aryl iodo and diiodo compounds with unactivated alkyl alkynes and terminal dialkynes to produce various novel symmetrical dialkynes and disubstituted internal alkynes in excellent yields.

18 Claims, 1 Drawing Sheet

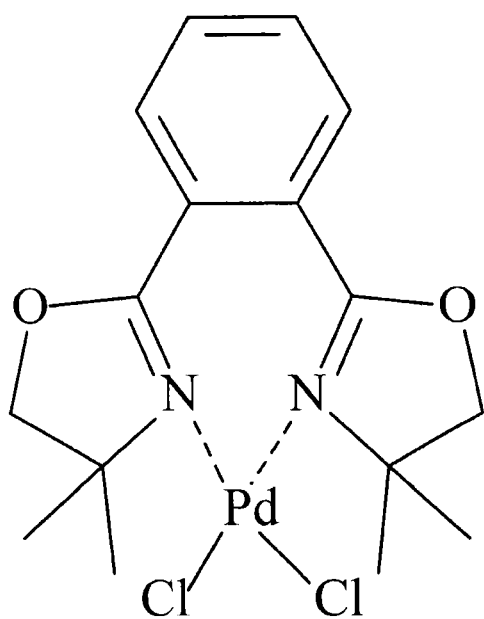

PALLADIUM(II) COMPLEX FOR CATALYZING SONOGASHIRA COUPLING REACTIONS AND A METHOD THEREOF

STATEMENT OF FUNDING ACKNOWLEDGEMENT

This project was funded by the National Plan for Science, Technology and Innovation (MARIFAH)—King Abdulaziz City for Science and Technology—through the Science & Technology Unit at King Fahd University of Petroleum & Minerals (KFUPM), the Kingdom of Saudi Arabia, award number (11-PET1665-04).

BACKGROUND OF THE INVENTION

Technical Field

The present disclosure relates to a palladium(II) complex which catalyzes the Sonogashira coupling reaction efficiently under mild reaction conditions and a method of employing the palladium(II) complex to synthesize internal alkynes.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

The Sonogashira coupling of aryl halides with aryl and alkyl alkynes provides a powerful tool for construction of the carbon-carbon bond between acetylenes and alkenes/arenes (Lui, C.; Bao, F.; Ni, Q. Arkivoc xi, 2011, 60. Guan, J. T.; Weng, T. Q.; Yu, G.; Liu, S. H. Tetrahedron Lett. 2007, 48, 7129. Komaromi, A.; Novak, Z. Chem. Comm. 2008, 4968. Huang, H.; Liu, H.; Jiang, H.; Chen, K. J. Org. Chem. 2008, 73, 6037. Gu, Z.; Li, Z.; Liu, Z.; Wang, Y.; Liu, C.; Xiang, J. Catal. Comm. 2008, 9, 2154. Casado, M. A.; Fazal, A.; Oro, L. A. Arab. J. Sc. Eng. 2013, 38, 1631, each incorporated herein by reference in their entirety). Alkynes are important because they are found in a wide range of natural products and other biologically active substances, and they are versatile intermediates for the production of materials for advanced engineering applications such as conducting polymers, non-linear optical devices and liquid crystals (Leadbeater, N. E.; Tominack, B. J. Tetrahedron. 2003, 44, 8653. Hamajima, A.; Isobe, M.; Org. Lett. 2006, 8, 1205. Mujahidin, D.; Doye, S. Eur. J. Org. Chem. 2005, 2689. Hajipour, A. R.; Zade, Z. S.; Azizi, G. Appl. Organometal. Chem. 2014, 28, 696, each incorporated herein by reference in their entirety).

The development of methods for incorporating C—C triple bonds into molecules remains an important area of research (Mathias, E.; Gregory, C. F. J. Am. Chem. Soc. 2003, 125, 13642, incorporated herein by reference in its entirety). In general, the Sonogashira coupling, which is the most commonly used method for the production of internal alkynes, is catalyzed by palladium complexes in combination with copper salts, and a large excess of an amine base (Chinchilla, R.; Najera, C. Chem. Rev. 2007, 107, 874, incorporated herein by reference in its entirety). However, the presence of copper(I) co-catalysts can result in the in situ formation of copper(I) acetylides leading to the oxidative homocoupling of alkynes (Siemsen, P.; Livingstone, R. C.; Diederich, F. Angew. Chem. Int. Ed. 2000, 39, 2633. Bakherad, M.; Keivanloo, A.; Bahramian, B.; Jajarmi, S. Appl. Catal. A: General 2010, 390, 135, each incorporated herein by reference in their entirety). To avoid homocoupling reactions, serious efforts have been made, including the employment of new, active palladium complexes as catalysts. However, there are problems associated with the copper-free systems such as the frequent requirement for high palladium catalysts loading, excess of base and rigorously dried organic solvent (Hundertmark, T.; Littke, A. F.; Buchwald, S. L.; Fu, G. C. Org. Lett. 2000, 2, 1729. Eckhardt, M.; Fu, G. C. J. Am. Chem. Soc. 2000, 39, 2632, each incorporated herein by reference in their entirety).

Through a comparison of available literature reports describing the use of phosphorous ligands in copper-free Sonogashira reactions, it was found that there are limited studies on the use of palladium-nitrogen catalyst systems (Tykwinski, R. R. Angew. Chem. Int. Ed. 2003, 42, 1566. Feuerstein, M.; Doucet, H.; Santelli, M. Tetrahedron Lett. 2004, 45, 8443. Liang, Y.; Xie, Y.; Li, J. J. Org. Chem. 2006, 71, 379. Valishina, E. A.; Silva, M. F. C.; Kinzhalov, M. A.; Timofeeva, S. A.; Buslaeva, T. M.; Haukka, M.; Pombeiro, A. J. L.; Boyarskiy, V. B.; Kukusukin, V. Y.; Luzyanin. K. V. J. Mol. Catal. A: Chemical. 2014, 395, 162. Soheili, A.; Walker, J. A.; Murry, J. A.; Dormer, P. G.; Hughes, D. L. Org. Lett. 2003, 5, 22, 4191. Liang, B.; Dai, M.; Chen, J.; Yang, Z. J. Org. Chem., 2005, 70, 391. John, A.; Shaikh, M. M.; Ghosh, P. Dalton. Trans. 2009, 10581. Dash, C.; Shaikh, M. M.; Ghosh, P. Eur. J, Inorg. Chem. 2009, 1608, each incorporated herein by reference in their entirety). Moreover, such catalyst systems utilize a high temperature, a longer reaction time, a relatively high palladium catalyst loading, a phosphine ligand, copper as co-catalyst, or a phase transfer agent (Najera, C.; Motto, J. G.; Karlstrom, S.; Falvello, L. R. Org. lett. 2003, 5, 1451. Buchmeiser, M. R.; Schareina, T.; Kempe, R.; Wurst, K. J. Organometal. Chem. 2001, 634, 39. Wang, D.; Denux, J.; Astruc, D. Adv. Synth. Catal. 2013, 355, 129. Lin, B-N.; Huang, S-H.; Wu, W-Y.; Mou, C-Y, Tsai, F-Y. Molecule 2010, 15, 9157. Aljarin, M.; Leonardo, C. L.; Lorente, P. L.; Raja, R.; Bautista, D.; Orenes, R-A. Dalton. Trans. 2012, 41, 12259, each incorporated herein by reference in their entirety). Furthermore, many of the reported phosphine-free and copper-free systems are limited to the coupling of aryl iodides with aryl alkynes (Ghiaci, M.; Zarghani, M.; Moeinpour, F.; Khojastehnezhad, A. Appl. Organometal. Chem. 2014, 28, 589, incorporated herein by reference in its entirety).

Therefore, an object of the present disclosure is to provide a palladium(II) catalyst effective for Sonogashira coupling reactions which are carried out in the absence of copper(I) catalysts and phosphine ligands. It is a further object to provide a method of employing the palladium(II) catalyst.

BRIEF SUMMARY

A first aspect of the disclosure relates to a palladium(II) complex of formula (I):

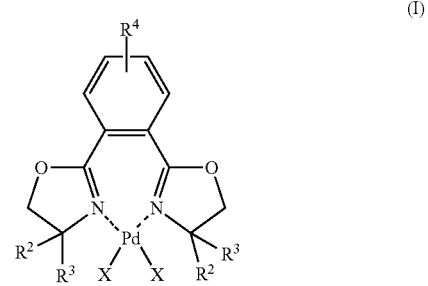

(I)

wherein $R^2$, $R^3$, and $R^4$ are each independently a hydrogen atom, an optionally substituted alkyl group, or an optionally substituted aryl group, and X is I, Br, Cl, OTf, or OAc.

In one embodiment, $R^2$ and $R^3$ are methyl groups, $R^4$ is a hydrogen atom, a methyl group or a nitro group, and X is Cl, Br, or OAc.

In one embodiment, the palladium(II) complex is:

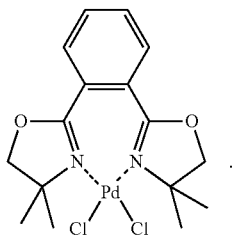

A second aspect of the disclosure relates to a method for preparing a compound of formula Ar—C≡C—$R^1$, the method comprising reacting a compound of formula ArY with a compound of formula HC≡C$R^1$ in the presence of a solvent, a base, and a palladium(II) complex of formula (I):

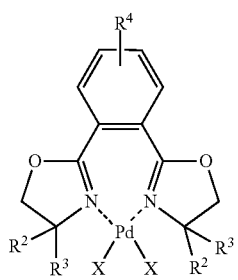

(I)

thereby yielding the compound of formula Ar—C≡C—$R^1$, wherein Ar is an optionally substituted aryl group, Y is I, Br, Cl, OTf, or OTs, $R^1$ is an optionally substituted alkyl group, or an optionally substituted aryl group, $R^2$, $R^3$, and $R^4$ are each independently a hydrogen atom, an optionally substituted alkyl group, or an optionally substituted aryl group, and X is I, Br, Cl, OTf, or OAc.

In one embodiment, the method is performed in air, in the absence of a phosphine and in the absence of a copper(I) complex.

In one embodiment, the compound of formula ArY is an aryl monohalide or an aryl dihalide.

In one embodiment, the compound of formula ArY is at least one selected from the group consisting of iodobenzene, 4-iodoaniline, 4-iodoacetophenone, 4-iodobenzonitrile, 4-iodoanisole, 1-iodo-4-nitrobenzene, and 1,4-diiodobenzene.

In one embodiment, the compound of formula HC≡C$R^1$ is a monoalkyne or a dialkyne.

In one embodiment, the compound of formula HC≡C$R^1$ is at least one monoalkyne selected from the group consisting of phenylacetylene, 4-ethynylaniline, 4-ethynylbenzaldehyde, 4-ethynyltoluene, 4-ethynyl-α,α,α-trifluorotoluene, 1-hexyne, 1-octyne, 1-decyne, 1-dodecyne, 4-phenyl-1-butyne, 5-phenyl-1-pentyne, 5-chloro-1-pentyne, 5-hexyenitrile, 3,3-dimethyl-1-butyne, ethynyltrimethylsilane, (triphenylsilyl)acetylene, 4-(tert-butyldimethylsilyloxy)-1-butyne, 3,4-dimethyl-1-pentyn-3-ol, 1-hexyne, and 3,5-dimethyl-1-hexyn-3-ol, or at least one dialkyne selected from the group consisting of 1,4-diethynylbenzene, 1,3-diethynylbenzene, or 1,7-octadiyne.

In one embodiment, a molar ratio of the compound of formula ArY to the compound of formula HC≡C$R^1$ ranges from 2:1 to 2:15.

In one embodiment, a molar ratio of the base to the compound of formula ArY ranges from 1:1 to 8:1.

In one embodiment, the molar ratio of the base to the compound of formula ArY ranges from 2:1 to 4:1.

In one embodiment, an amount of the palladium(II) complex ranges from 0.1-10 mol % relative to a number of moles of the compound of formula ArY.

In one embodiment, the amount of the palladium(II) complex ranges from 1-5 mol % relative to the number of moles of the compound of formula ArY.

In one embodiment, the solvent comprises 5-95% by volume of water and 5-95% by volume of an organic solvent, based on a total volume of the solvent.

In one embodiment, the solvent consists of 50% by volume of water and 50% by volume of the organic solvent, based on the total volume of the solvent.

In one embodiment, the organic solvent is at least one selected from the group consisting of methanol, dimethyl formamide, and acetonitrile.

In one embodiment, the organic solvent is acetonitrile.

In one embodiment, the base is at least one selected from the group consisting of an alkali metal hydroxide, an alkali metal carbonate, and an amine.

In one embodiment, the reacting is performed at a temperature ranging from 18-60° C.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1 is an embodiment of the palladium(II) catalyst of formula (I) employed in Sonogashira coupling reactions.

DETAILED DESCRIPTION OF THE EMBODIMENTS

Embodiments of the present disclosure will now be described more fully hereinafter with reference to the accompanying drawings, in which some, but not all of the embodiments of the disclosure are shown.

The present disclosure will be better understood with reference to the following definitions.

As used herein, the words "a" and "an" and the like carry the meaning of "one or more".

As used herein, the terms "compound" and "complex" are used interchangeably, and are intended to refer to a chemical entity, whether in the solid, liquid or gaseous phase, and whether in a crude mixture or purified and isolated.

The term "alkyl", as used herein, unless otherwise specified, refers to a straight, branched, or cyclic hydrocarbon fragment. Non-limiting examples of such hydrocarbon fragment include methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, vinyl, allyl, 1-propenyl, 2-propenyl, 1-butenyl, 2-butenyl, 3-butenyl, 1,-pentenyl, 2-pentenyl, 3-pentenyl, 4-pentenyl, 1-hexenyl, 2-hexenyl, 3-hexenyl, 4-hexenyl, or 5-hexenyl. As used herein, the term "cyclic hydrocarbons" refers to cyclized alkyl groups. Exemplary cyclic hydrocarbon (i.e. cycloalkyl) groups include, but are not limited to, cyclopropyl, cyclobutyl, cyclopentyl, cyclohexyl, norbornyl, and adamantyl. Branched cycloalkyl groups, such as exemplary 1-methylcyclopropyl and 2-methycyclopropyl groups, are included in the definition of cycloalkyl as used in the present disclosure.

The term "aryl", as used herein, and unless otherwise specified, refers to phenyl, biphenyl, naphthyl, anthracenyl, and includes heteroaryl that can be furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl, (or its N-oxide), thienyl, pyrimidinyl (or its N-oxide), 1H-indolyl, isoquinolyl (or its N-oxide) or quinolyl (or its N-oxide).

As used herein, the term "substituted" refers to at least one hydrogen atom that is replaced with a non-hydrogen group, provided that normal valencies are maintained and that the substitution results in a stable compound. When a compound or a R group (denoted as $R^1$, $R^2$, and so forth) is noted as "optionally substituted", the substituents are selected from the exemplary group including, but not limited to, halo, hydroxy, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl, or arylakyl), alkanylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamido (e.g. —$SO_2NH_2$), substituted sulfonamide, nitro, cyano, carboxy, carbamyl (e.g. —$CONH_2$), substituted carbamyl (e.g. —CONHalkyl, —CONHaryl, —CONHarylalkyl or cases where there are two substituents on one nitrogen from alkyl, aryl, or arylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety).

As used herein, "derivative" refers to a chemically modified version of a chemical compound that is structurally similar to a parent compound.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

This disclosure relates to an active palladium(II) complex for the Sonogashira coupling reactions of aryl halides, aryl triflates, or aryl tosylates with terminal aryl and alky alkynes under mild reaction conditions, and preferably in the absence of copper catalysts and phosphine ligands.

Therefore, a first aspect of the disclosure relates to a palladium(II) complex of formula (I):

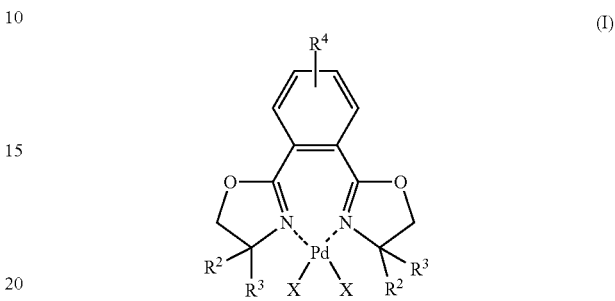

wherein $R^2$, $R^3$, and $R^4$ are independently a hydrogen atom, an optionally substituted alkyl group, or an optionally substituted aryl group, and X is I, Br, Cl, OTf, or OAc. The optionally substituted alkyl group may comprise 1-8 carbon atoms, preferably 1-5 carbon atoms, more preferably 1-3 carbon atoms. In one embodiment, the optionally substituted alkyl group comprises 1 carbon atom and is a methyl group. The optionally substituted aryl group is preferably a phenyl group. The alkyl and aryl groups may be substituted with the aforementioned substituents. Preferably, the alkyl and/or the aryl groups are substituted with hydroxyl, alkoxy, aryloxy, nitro, or cyano, either unprotected, or protected as necessary.

In another embodiment, $R^2$, $R^3$, and $R^4$ may be independently a halogen atom, a hydroxyl, a nitro, a cyano, an optionally substituted heterocyclyl, an optionally substituted arylalkyl, an optionally substituted heteroaryl, or an optionally substituted alkoxyl. The optionally substituted heterocyclyl may be a derivative of an O-heterocyclyl such as tetrahydrofuran, tetrahydropyran, or dioxane. The optionally substituted heteroaryl may be a derivative of an O-heteroaromatic compound such as furan. The optionally substituted arylalkyl may be, but is not limited to, benzyl, phenethyl, and phenylpropyl. The optionally substituted alkoxyl may be, but is not limited to, methoxy, ethoxy, and phenoxyl.

In some embodiments, when $R^2$ and $R^3$ are different, and either $R^2$ or $R^3$ is a hydrogen atom, the ligand is chiral and has two enantiomers. Either enantiomer may be employed in the present disclosure. As used herein, the term "ligand" refers to an organic molecule comprising a phenyl ring, and two oxazoline groups bound separately to the phenyl ring via a C—C bond and arranged ortho to one another, and each oxazoline group comprises a nitrogen atom bound to the palladium(II) ion covalently.

In some embodiments, $R^2$ and $R^3$ may not be an amino, an alkylamino, an arylamino, a N-monosubstituted amino, a N,N-disubstituted amino, a thiol or an optionally substituted thioalkoxyl because these groups contain nucleophilic atoms that may poison the catalyst. As used herein, the term "poisoning" refers to the nucleophilic atom(s) coordinating strongly to the palladium ion and thereby reducing the effectiveness of the catalyst.

The group $R^4$ may be located ortho or meta to one of the oxazolyl groups. Preferably, $R^4$ is located meta to one of the oxazolyl groups.

In some embodiments, $R^2$ and $R^3$ are methyl groups, $R^4$ is a methyl group, a nitro group, or a hydrogen atom, and X is Cl, Br or OAc. Preferably, the palladium(II) complex is:

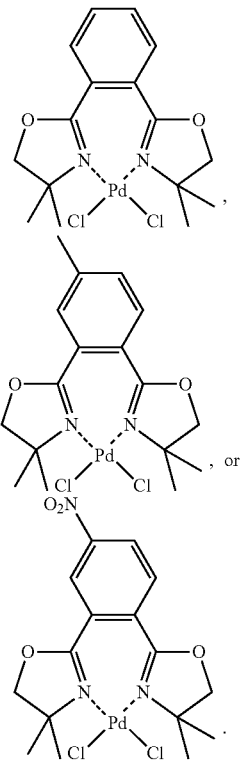

More preferably, the palladium(II) complex is 2,2'-(1,2-phenylene)bis(4,4-dimethyl-4,5-dihydrooxazole)-N,N'-dichloridopalladium(II), abbreviated Pd-BOX, with the following structure:

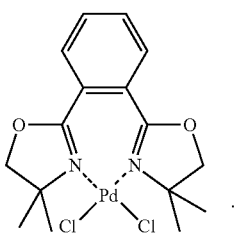

A preparation of the ligand is described hereinafter. In a preferred embodiment, a solution of phthalonitrile and zinc triflate in dried chlorobenzene is stirred at room temperature for 15 min. In some embodiments, phthalonitrile is substituted and comprises the aforementioned substituents. For example, 4-methylphthalonitrile or 4-nitrophthalonitrile may be used. An amount of phthalonitrile or substituted phthalonitrile ranges from 1-20 mmol, preferably 1-10 mmol, more preferably 1-5 mmol. In some embodiments, other triflate salts such as lanthanide triflates of the formula $Ln(OTf)_3$ (where Ln=La, Ce, Pr, Nd, Sm, Eu, Gd, Tb, Dy, Ho, Er, Tm, Yb, Lu, Y) and scandium triflate are used. An amount of triflate salt ranges from 0.1-1 mmol, preferably 0.1-0.5 mmol, more preferably 0.1-0.3 mmol, and 1-10 mol % relative to the number of moles of the optionally substituted phthalonitrile, preferably 1-8 mol %, more preferably 3-6 mol %. Exemplary organic solvents include, but are not limited to, benzene, toluene, p-xylene, o-xylene, and m-xylene. An amount of the organic solvent ranges from 5-50 ml, preferably 10-40 ml, more preferably 20-40 ml. The solution may be stirred for 5-60 minutes, preferably 5-30 minutes, more preferably 10-20 minutes at a temperature ranging from 10-40° C., preferably 15-30° C., more preferably 20-30° C.

A solution of 2-amino-1-propanol in dried chlorobenzene was slowly added to the solution of phthalonitrile and zinc triflate in dried chlorobenzene to form a reaction mixture. An amount of the 2-amino-1-propanol ranges from 1-40 mmol, preferably 1-30 mmol, more preferably 1-15 mmol, and a molar ratio of 2-amino-1-propanol to phthalonitrile ranges from 1:1 to 20:1, preferably 1:1 to 10:1, more preferably 1:1 to 5:1. The 2-amino-1-propanol may be further substituted and comprise the aforementioned substituents on C-1, C-2, or both, and may be a chiral reagent, an achiral reagent, or a racemic mixture. Preferably, an achiral 2-amino-2-methyl-1-propanol is used. In other embodiments, a chiral ligand is prepared by employing only one of the enantiomers of 2-amino-1-propanol (or further substituted 2-amino-1-propanol), such as (S)-(+)-2-amino-1-propanol or (R)-(−)-2-amino-1-propanol.

The temperature of the reaction mixture was raised to 80-160° C., preferably 100-160° C., more preferably 110-140° C. and refluxed for 12-48 hours, preferably 18-48 hours, more preferably 18-36 hours. The ligand of the reaction is isolated and purified by methods known to those skilled in the art, such as filtration through a celite containing cartridge, aqueous work-up, extraction with organic solvents, distillation, crystallization, column chromatography, and high pressure liquid chromatography (HPLC) on normal phase or reversed phase. Preferred methods include, extraction with organic solvents and column chromatography, but are not limited to those exemplified. The yield of the ligand is at least 50%, preferably at least 75%, more preferably at least 80%.

A preparation of the palladium(II) complex is described hereinafter. In a preferred embodiment, a solution of the aforementioned ligand (0.5 mmol) and bis(benzonitrile)-palladium(II) chloride (0.5 mmol) in dried DMF (8.0 ml) was stirred at room temperature for 6 h. An amount of the ligand ranges from 0.1-5 mmol, preferably 0.1-3 mmol, more preferably 0.1-1 mmol. Exemplary palladium salts include, but are not limited to, bis(acetonitrile)-palladium(II) chloride and palladium(II) chloride. An amount of the palladium(II) salt ranges from 0.1-5 mmol, preferably 0.1-3 mmol, more preferably 0.1-1 mmol. A molar ratio of the ligand to the palladium(II) salt ranges from 1:1 to 1:2, preferably 1:1 to 2:3, more preferably 1:1 to 1:1.2. Exemplary organic solvents include, but are not limited to, toluene, benzene, dimethyl sulfoxide, and tetrahydrofuran. An amount of the solvent ranges from 1-15 ml, preferably 1-10 ml, more preferably 5-10 ml. The reaction mixture may be stirred for 1-24 hours, preferably 1-10 hours, more preferably 3-7 hours at a temperature ranging from 10-40° C., preferably 15-30° C., more preferably 20-30° C. The palladium(II) salt is isolated and purified by the aforementioned methods. The yield of the palladium(II) complex is at least 50%, preferably at least 75%, more preferably at least 80%.

This disclosure also relates to an efficient method for the synthesis of internal alkynes from the Sonogashira coupling reaction. The disclosed copper-free and phosphine-free catalytic system provides a significant advantage in terms of activity, selectivity, and tolerance to various functional groups on both the aryl halide/triflate/tosylate and the alkyne.

Novel compounds, such as 1,3-bis(phenylethynyl)benzene (4ag, Example 7, Table 3, entry 2), 6-phenylhex-5-ynenitrile (6ah, Example 8, Table 4, entry 8), 6,6'-benzene-1,4-diylbishex-5-ynenitrile (7gg, Example 10, Table 5, entry 5), 1,4-bis(5-chloropent-1-yn-1-yl)benzene (7gh, Example 10, Table 5, entry 4) and 1,4-bis(3,5-dimethyl-1-hex-1-yn-3-ol)benzene (7go, Example 10, Table 5, entry 7), are prepared with the disclosed method. These new compounds could be of high interest to companies in the fields of polymer, petrochemical and chemical feedstock, and electronic display. For example, the bis(phenylethynyl)-benzene (BPEB) derivatives shown in Example 7, table 3 can be very useful and attractive precursors in the synthesis of liquid crystals for electronic displays.

Therefore, a second aspect of the disclosure relates to a method for preparing a compound of formula Ar—C≡C—R$^1$, the method comprising reacting a compound of formula ArY with a compound of formula HC≡CR$^1$ in the presence of a solvent, a base, and a palladium(II) complex of formula (I):

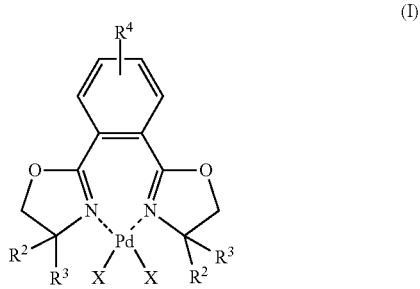

thereby yielding the compound of formula Ar—C≡C—R$^1$, wherein Ar is an optionally substituted aryl group, Y is I, Br, Cl, OTf, or OTs, R$^1$ is an optionally substituted alkyl group, or an optionally substituted aryl group, R$^2$, R$^3$, and R$^4$ are independently a hydrogen atom, an optionally substituted alkyl group, or an optionally substituted aryl group, and X is I, Br, Cl, OTf, or OAc.

The aforementioned description of the palladium(II) complex of formula (I) in the first aspect of the disclosure is also relevant to the palladium(II) complex of formula (I) in the second aspect of the disclosure.

The presence of copper(I) co-catalysts in a typical Sonogashira coupling reaction can result in the in situ formation of copper(I) acetylides, which leads to the oxidative homocoupling of alkynes thereby decreasing the yield of the coupling product (Siemsen, P.; Livingstone, R. C.; Diederich, F. Angew. Chem. Int. Ed. 2000, 39, 2633. Bakherad, M.; Keivanloo, A.; Bahramian, B.; Jajarmi, S. Appl. Catal. A: General 2010, 390, 135, each incorporated herein by reference in their entirety). The use of phosphine ligands, which are usually sensitive to air and moisture, often restricts the reaction to inert atmospheres. Therefore, preferably, the method is performed in an oxygen-containing atmosphere, and in the absence of a copper(I) complex and a phosphine ligand to overcome these limitations. Specifically, the disclosed palladium(II) catalyst is stable in air and moisture, thus allowing the reactions to be conducted in the oxygen-containing atmosphere. Also, there is minimal homocoupling of the alkyne because copper catalysts are not employed. An amount of homocoupled alkyne may range from 0-10% by weight of an initial amount of the alkyne, preferably 0-3% by weight, more preferably 0-1% by weight. The oxygen-containing atmosphere comprises oxygen, and may comprise other gases, such as nitrogen, argon, carbon dioxide, and water vapor. An amount of oxygen ranges from 1-30% by volume, preferably 10-30%, more preferably 15-25% of the total volume of the atmosphere.

The group Ar is an optionally substituted aryl group and may comprise the aforementioned substituents. Preferably, the aryl group is phenyl. In a preferred embodiment, the substituents are electron-donating groups such as amino, alkoxyl, and alkyl. In another preferred embodiment, the substituents are electron-withdrawing groups such as nitro, cyano, and acetyl. The aryl group may comprise up to 5 substituents. Preferably, there is one substituent. The substituent may be located ortho, meta or para to Y. Preferably, the substituent is located para to Y.

The compound of formula ArY may be an aryl monohalide such as aryl chloride, aryl bromide, and aryl iodide. Preferably, the aryl monohalide is an aryl iodide such as iodobenzene. Non-limiting examples of aryl monohalides include iodobenzene, 4-iodoaniline, 4-iodoacetophenone, 4-iodobenzonitrile, 4-iodoanisole, and 1-iodo-4-nitrobenzene.

In another embodiment, the compound of formula ArY may be an aryl dihalide such as 1,4-dichlorobenzene, 1,4-dibromobenzene, and 1,4-diiodobenzene. Preferably, the aryl halide is 1,4-diiodobenzene.

The group R$^1$ may be an optionally substituted alkyl group. The optionally substituted alkyl group may comprise 3-20 carbon atoms, preferably 4-15 carbon atoms, more preferably 6-12 carbon atoms. The optionally substituted alkyl group may be substituted with the aforementioned substituents. Preferably, the substituents are cyano, halo, hydroxyl, silane and derivatives thereof, silyl ether and derivatives thereof, phenethyl, and phenylpropyl.

The group R$^1$ may be an optionally substituted aryl group. The optionally substituted aryl group is preferably a phenyl group. The optionally substituted aryl group may be substituted with the aforementioned substituents. Preferably, the substituents are amino, trifluromethyl, and formyl.

In one embodiment, the compound of formula HC≡CR$^1$ is a monoalkyne, which may be aliphatic or aromatic. Non-limiting examples of aliphatic monoalkynes include acetylene, 1-hexyne, 1-octyne, 1-decyne, 1-dodecyne, 4-phenyl-1-butyne, 5-phenyl-1-pentyne, 5-chloro-1-pentyne, 5-hexynenitrile, 3,3-dimethyl-1-butyne, ethynyltrimethylsilane, (triphenylsilyl)acetylene, 4-(tert-butyldimethylsilyloxy)-1-butyne, 3,4-dimethyl-1-pentyn-3-ol, 1-hexyne, and 3,5-dimethyl-1-hexyn-3-ol. Non-limiting examples of aromatic monoalkynes include phenylacetylene, 4-ethynylaniline, 4-ethynylbenzaldehyde, 4-ethynyltoluene, and 4-ethynyl-α,α,α-trifluorotoluene.

In some embodiments, the compound of formula HC≡CR$^1$ is a dialkyne, which may be aliphatic or aromatic. Non-limiting examples of aliphatic dialkynes include 1,5-hexadiyne, 1,6-heptadiyne, and 1,7-octadiyne. Preferably, 1,7-octadiyne is employed in the method. Non-limiting examples of aromatic dialkynes include 1,4-diethynylbenzene and 1,3-diethynylbenzene. These aromatic dialkynes are precursors to bis(phenylethynyl)-benzene (BPEB) derivatives, which are important components of liquid crystals for electronic displays. They are widely employed in the production of notebook computer screens, mobile phones, flat screen monitors and LCD televisions (Beeby, A.; Findlay, K.; Low P. J.; Marder T. B. A. J. Am. Chem. Soc. 2002, 124, 8280.s. Schwab P. F. H.; Smith, J. R.; Michl, J. Chem. Rev. 2005, 105, 1197, each incorporated herein by reference in their entirety). BPEBs are characterized by high clearing and melting point, as well as large optical anisotropy values (Tanaka T.; Sekine, C.; Ashida, T.; Ishitobi, M.; Konya, N.; Minai, M.; Fujisawa, K. Liq. Cryst. 2000, 346, 209. Liao, Y. M.; Chen, H. L.; Hsu, C. S.; Gauza, S.; Wu, S. T. Liq. Cryst. 2007, 34, 507. Li, N.; Li, Z.; Zhang, X.; Hua, R. Int. J. Mol. Sci. 2013, 14:12, 23257, each incorporated herein by reference in their entirety). The disclosed method was successfully applied to the synthesis of BPEB derivatives (Example 7, Table 3).

A molar ratio of the compound of formula ArY to the compound of formula $HC \equiv CR^1$ may range from 2:1 to 2:15, preferably 2:1 to 2:10, more preferably 2:1 to 2:6. Preferably, the molar ratio ranges from 2:1 to 2:4, preferably 2:1 to 2:3 when ArY is an aryl monohalide. In another preferred embodiment, the molar ratio ranges from 2:4 to 2:7, preferably 2:4 to 2:5 when ArY is an aryl dihalide.

An amount of the palladium(II) complex may range from 0.1-10 mol % of a number of moles of the compound of formula ArY, preferably 1-5 mol %, more preferably 1-2 mol %, although higher catalyst loadings (up to 20 mol %, up to 30 mol %, etc.) may be used and the method will still proceed as intended.

The solvent may comprise 5-95% by volume of water and 5-95% by volume of an organic solvent, based on a total volume of the solvent. Preferably, the solvent comprises 30-70% by volume of water and 30-70% by volume of an organic solvent, based on the total volume of the solvent. Most preferably, the solvent consists of 50% by volume of water and 50% by volume of the organic solvent, based on the total volume of the solvent. Distilled water, doubly distilled water, deionized water, or deionized distilled water may be used. Preferably, deionized distilled water is used. Non-limiting examples of the organic solvents include dimethyl formamide, ethers, glycol ethers, acetamide, dimethyl acetamide, dimethyl sulfoxide, dioxane, tetrahydrofuran, acetonitrile, an alcohol, such as methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol,3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol, and combinations thereof. Preferably, the organic solvent is acetonitrile.

The presence of a base is often important for the palladium-catalyzed Sonogashira coupling reaction in order to neutralize the hydrogen halide produced as the byproduct of the coupling reaction (Chih-chung, T.; Mungyuen, L.; Bingli, M.; Sarah, W.; Alan, S. C.; Chem. Lett. 2011, 40:9 955. Thorwirth, R.; Stolle, A.; Ondruschka, B.; Green Chem. 2010, 12, 985. Bakherad, M.; Keivanloo, A.; Samangooei, S.; Omidian, M. J. Organometal. Chem. 2013, 740, 78. Feng, Z.; Yu, S.; Shang, Y. Appl. Organometal. Chem. 2008, 22, 577. Shingo, A.; Motohiro, S.; Yuki, S.; Hirojiki, S.; Takuya, Y.; Aiky, O. Chem. Lett. 2011, 40:9, 925. Korzec, M.; Bartczak, P.; Niemczyk, A.; Szade, J.; Kapkowski, M.; Zenderowska, P.; Balin, K.; Lelarko, J.; Polariski, J. J. Catal. 2014, 313, 1. Zhang, G.; Luan, Y.; Han, X.; Wang, Y.; Wen, X.; Ding, C. Appl. Organometal. Chem. 2014, 28, 332, each incorporated herein by reference in their entirety). The base may be an alkali metal hydroxide, such as LiOH, KOH, and NaOH, an alkali metal carbonate, such as $Li_2CO_3$, $K_2CO_3$, and $Na_2CO_3$, or an amine such as trimethylamine, piperidine, and diethylamine. A molar ratio of the base to the compound of formula ArY may range from 1:1 to 8:1, preferably 1:1 to 5:1, more preferably 2:1 to 4:1. Preferably, the molar ratio ranges from 1:1 to 3:1, preferably 1.5:1 to 2.5:1, when ArY is an aryl monohalide. In another preferred embodiment, the molar ratio ranges from 3:1 to 5:1, preferably 3.5:1 to 4.5:1 when ArY is an aryl dihalide.

Prior to the reacting, the method comprises an adding step where the palladium(II) complex is added to the organic solvent, followed by the compounds of formulae ArY and $HC \equiv CR^1$, the base, and water to form a reaction mixture. In another embodiment, the base is first dissolved in water to form a basic solution, which is then added to the other compounds in the organic solvent. In one embodiment, the catalyst is not preformed but is formed in situ in a reaction flask (i.e. at least one of the aforementioned palladium(II) salts and the ligand are added to the reaction flask separately). Preferably, the adding step is performed in air. In another embodiment, the adding step is performed in an inert atmosphere provided by inert gases such as argon, nitrogen, and helium.

The reacting may be performed at a temperature ranging from 18-60° C., preferably 18-40° C., more preferably 18-25° C. An external heat source, such as a water bath or an oil bath, an oven, or a heating mantle, may be employed to heat the reaction mixture. In a preferred embodiment, the external heat source is a thermostatted thermocirculator. In one embodiment, the aqueous solution is not heated with microwave irradiation. Preferably, the reacting is performed in air. In another embodiment, the reacting is performed in an inert atmosphere provided by the aforementioned inert gases.

A duration of the reaction may range from 0.5-10 hours, preferably 0.5-6 hours, more preferably 0.5-3 hours. The reaction may be stirred throughout the duration of the reaction by employing a magnetic stirrer or an overhead stirrer. In another embodiment, the reaction mixture is left to stand (i.e. not stirred).

The progress of each reaction may be monitored by methods known to those skilled in the art, such as thin layer chromatography, gas chromatography, nuclear magnetic resonance, infrared spectroscopy, and high pressure liquid chromatography combined with ultraviolet detection or mass spectroscopy. Preferably, thin layer chromatography and gas chromatography combined with mass spectroscopy are used.

The compounds obtained by the method of the present disclosure are isolated and purified by employing the aforementioned methods which are well-known to those skilled in the art. The isolated yield of the compound of formula $ArC \equiv CR^1$ is at least 87%, preferably at least 90%, more preferably at least 92%.

Having generally described this disclosure, a further understanding can be obtained by reference to certain specific examples which are provided herein for purposes of illustration only and are not intended to be limiting unless otherwise specified.

Example 1

Reagents and Experimental Methods

Reagents for the synthesis of ligands and palladium(II) complexes were purchased from Sigma Aldrich and were used as received. All solvents used in the synthesis were distilled before use. The products were purified using flash column chromatography with 60 F silica gel from Fluka Chemie AG (Buchs, Switzerland). $^1$H NMR and $^{13}$C NMR spectral data were obtained using a 500 MHz NMR instrument (Joel 1500 model). Chemical shifts were recorded in ppm using tetramethylsilane as reference and CDCl$_3$ as solvent. IR spectra were recorded in wavenumbers (cm$^{-1}$) using an FT-IR spectrometer (PerkinElmer 16 F model). Elemental analyses were performed with a PerkinElmer Series 11 (CHNS/O) Analyzer 2400. Merck 60 F$_{254}$ silica gel plates (250 μm layer thickness) were used for TLC analyses. A Varian Saturn 2000 GC-MS instrument was used to analyze the products. GC (Agilent 6890) was adopted to monitor the reactions.

Example 2

Synthesis of 2,2-(1,2-Phenylene)bis(4,4-Dimethyl-4,5-Dihydrooxazole)

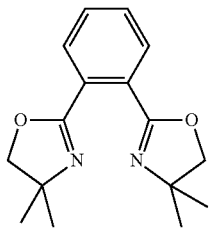 [SMILES: CC1(C)COC(c2ccccc2C2=NC(C)(C)CO2)=N1]

A solution of phthalonitrile (4.0 mmol) and zinc triflate (5.0 mol %, 0.2 mmol) in dried chlorobenzene (30 ml) was stirred at room temperature for 15 min. A solution of 2-amino-2-methyl-1-propanol (8.0 mmol) in dry chlorobenzene (5 ml) was slowly added. The temperature was raised to 135° C. and the reaction mixture was refluxed for 24 h. The product of the reaction, obtained as an oily residue, was dissolved in 30 ml of dichloromethane and extracted twice with distilled water (2×20 ml). The aqueous layer was then separated and the combined organic layers were dried with anhydrous sodium sulfate. The dichloromethane was removed using a rotary evaporator to obtain the impure product, which was then purified using silica gel column chromatography with dichloromethane-ether (4:1) as eluent (Ibrahim, M. B.; El Ali, B.; Fettouhi, M.; Ouahab, L. Appl. Organometal. Chem. 2015, 29, 400, incorporated herein by reference in its entirety).

Characterization data: colorless oil, isolated yield 82%. $^1$H NMR (500 MHz, CDCl$_3$, δ, ppm): 7.24 (dd, $^3$J=5.8 Hz, $^4$J=3.4 Hz, 2H, CH-4,5 arom.), 6.94 (dd, $^3$J=5.8 Hz, $^4$J=3.4 Hz, 2H, CH-3,6 arom.), 3.55 (s, 4H, OCH$_2$×2), 0.88 (s, 12H, CH$_3$×4). $^{13}$C NMR (125 MHz, CDCl$_3$, δ, ppm): 27.03 (CH$_3$×4), 66.81 (C×2), 72.80 (OCH$_2$×2), 127.64 (C-1,2 arom.), 128.56 (C-3,6 arom.), 129.11 (C-4,5 arom.), 161.12 (OCN). IR (ν, cm$^{-1}$): 2965, 1662, 1266, 1190. GC-MS (m/z): 273 (M+). Anal. Calcd. for C$_{16}$H$_{20}$N$_2$O$_2$ (272.35) (%): C, 70.56; H, 7.40; N, 10.29. Found (%): C, 70.51; H, 7.43; N, 10.23.

Example 3

Synthesis of 2,2'-(1,2-Phenylene)bis(4,4-Dimethyl-4,5-Dihydrooxazole)-N,N'-Dichloridopalladium(II) (Pd-BOX)

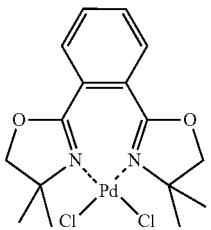

A solution of bis(oxazoline) ligand (0.5 mmol) and bis (benzonitrile)-palladium(II) chloride (0.5 mmol) in dried DMF (8.0 ml) was stirred at room temperature for 6 h. The solvent was removed under reduced pressure using a rotary evaporator. The crude product was then dissolved in dichloromethane at room temperature and layered with hexane. The product was obtained in the form of needle-shaped crystals. These pure crystals were separated, washed with diethyl ether, dried under vacuum and characterized using various spectroscopic techniques including $^1$H NMR, $^{13}$C NMR and IR spectroscopies, elemental analysis and X-ray diffraction analysis (Ibrahim, M. B.; El Ali, B.; Fettouhi, M.; Ouahab, L. Appl. Organometal. Chem. 2015, 29, 400, incorporated herein by reference in its entirety).

Characterization data: Pale yellow needle-shaped crystals; yield 81%; m.p. 252° C. $^1$H NMR (500 MHz, DMSO, δ, ppm): 7.88-8.00 (m, 4H, CH-3,4,5,6 arom.), 4.39 (s, 4H, OCH$_2$×2), 1.52 (s, 6H, NC(CH$_3$)$_2$), 1.57 (s, 6H, NC(CH$_3$)$_2$). $^{13}$C NMR (125 MHz, CDCl$_3$, δ, ppm): 27.8 (NC(CH$_3$)×4), 70.8 (NC), 80.5 (OCH$_2$), 125.5 (C-1,2 arom.), 129.5 (C-3,4 arom.), 132.9 (C-5,6 arom.), 163.9 (OCN). IR (KBr, ν, cm$^{-1}$): 2968, 1632, 1260, 1193. Anal. Calcd. for C$_{16}$H$_{20}$Cl$_2$N$_2$O$_2$Pd (449.67) (%): C, 42.74; H, 4.48; N, 6.23. Found (%): C, 42.71; H, 4.46; N, 6.29.

Example 4

General Procedure for Sonogashira Coupling Reaction

In a 10 mL round bottom flask, the palladium(II) complex (0.010 mmol) was dissolved in acetonitrile (2 mL). Aryl halide (1.0 mmol), alkyne (1.2 mmol), KOH (2.00 mmol) and distilled water (2 mL) were added. The mixture was stirred at room temperature (or 60° C.) for the required time. After reaction completion, the product was extracted with ethyl acetate (3×5 mL). The combined organic layers were dried with anhydrous sodium sulfate. The product was analyzed with GC and GC-MS. The product was purified using column chromatography with hexane-ethyl acetate as eluent (Ibrahim, M. B.; El Ali, B.; Malik, I.; Fettouhi, M. Tetrahedron Lett. 2016, 57, 554, incorporated herein by reference in its entirety). The characterization data for known products agreed with the data reported in literature.

Example 5

Varying the Parameters of Sonogashira Coupling Reaction

In order to determine the ideal conditions, several different experiments (Table 1) were performed at room temperature under aerobic conditions using iodobenzene and phenylacetylene as model substrates, and utilizing various palladium catalysts including the Pd-BOX complex. The effect of varying the solvent was investigated using the Pd-BOX complex shown in FIG. 1. Very low yield (15%) of 3aa was obtained when $CH_3OH$-water mixture was used as a solvent (Table 1, entry 1). The yield was slightly improved in DMF-$H_2O$ solvent mixture (Table 1, entry 2). Remarkably, changing of the solvent to $CH_3CN$—$H_2O$ led to excellent isolated yields (Table 1, entry 3).

Various bases such as KOH, NaOH, $K_2CO_3$, $Et_3N$ (Table 1, entries 3-6, 10-20) were tested. Excellent yields were obtained with KOH and NaOH, (94% and 90% respectively) (Table 1, entries 3 and 4). However, much lower yields were observed with $K_2CO_3$ and $Et_3N$ (60% and 47% respectively) (Table 1, entries 5 and 6).

During the studies, it was revealed that Pd-BOX (FIG. 1, Table 1, entry 3) provided excellent yields in comparison with commercially available palladium(II) complexes and salts (Table 1, entries 7-11).

It was found that the nature of the palladium complex had a pronounced impact on the reaction. The use of $Pd(OAc)_2$ (75%, Table 1, entry 8) gave slightly higher yields than $PdCl_2$ (69%, Table 1, entry 9), $PdCl_2$-Bipy (40%, Table 1, entry 10) and $PdCl_2$-Phen (20%, Table 1, entry 11).

TABLE 1

Reaction conditions for the palladium-catalyzed Sonogashira coupling reaction of iodobenzene with phenylacetylene.[a]

| Entry | Pd Complex | Solvent | Base | Yield (%)[b] |
|---|---|---|---|---|
| 1 | Pd-BOX | $CH_3OH$—$H_2O$ (1:1) | KOH | 15 |
| 2 | Pd-BOX | DMF—$H_2O$ (1:1) | KOH | 35 |
| 3 | Pd-BOX | $CH_3CN$—$H_2O$ (1:1) | KOH | 94 |
| 4 | Pd-BOX | $CH_3CN$—$H_2O$ (1:1) | NaOH | 90 |
| 5 | Pd-BOX | $CH_3CN$—$H_2O$ (1:1) | $K_2CO_3$ | 60 |
| 6 | Pd-BOX | $CH_3CN$—$H_2O$ (1:1) | $Et_3N$ | 47 |
| 7 | $PdCl_2$ | $CH_3CN$—$H_2O$ (1:1) | KOH | 69 |
| 8 | $Pd(OAc)_2$ | $CH_3CN$—$H_2O$ (1:1) | KOH | 75 |
| 9[c] | $PdCl_2$-Bipy | $CH_3CN$—$H_2O$ (1:1) | KOH | 40 |
| 10[c] | $PdCl_2$-Phen | $CH_3CN$—$H_2O$ (1:1) | KOH | 20 |
| 11 | $PdCl_2(PPh_3)_2$ | $CH_3CN$—$H_2O$ (1:1) | KOH | 43 |

[a]Reaction Conditions: Pd-catalyst (1 mol %), iodobenzene (1.0 mmol), phenylacetylene (1.5 mmol), base (2.0 mmol), solvent (4 ml), r.t., 2 h.
[b]Isolated yield.
[c]$PdCl_2$-BiPy = (2,2'-bipyridine)dichloridopalladium(II).
[d]$PdCl_2$-Phen = (1,10-phenanthroline)dichoridopalladium(II).

Example 6

Screening Aryl Iodides and Aryl Alkynes

Employing the reaction conditions listed in the Example 4, a range of aryl iodides was screened with an array of structurally and electronically different aryl alkynes (Table 2). With respect to the aryl iodides, both activated and deactivated aryl iodides reacted smoothly with alkynes bearing electron withdrawing and electron donating substituents and the cross-coupling products were obtained in excellent yields. The coupling of phenylacetylene with deactivated aryl iodides (Table 2, entries 2-5) afforded the internal acetylenes in high yields within 1 h. The coupling reactions of activated aryl iodides, such as 4-iodoanisole (Table 2, entry 6) and 4-iodoaniline (Table 2, entry 7), were completed within 3 h. The coupling of iodobenzene with activated aryl alkynes (Table 2, entries 8-10) afforded high yields of internal acetylenes within 3 h. The synthesis of 4,4'-diaminodiphenylacetylene was achieved in quantitative yield from the reaction of 4-iodoaniline with 4-ethynylaniline (Table 2, entry 11).

TABLE 2

Sonogashira coupling reactions of aryl iodides with aryl alkynes catalyzed by Pd-BOX.[a]

| Entry | R 1a-f | R' 2a-e | Time (h) | Yield (%)[b] 3aa-fe |
|---|---|---|---|---|
| 1 | H 1a | H 2a | 2 | 94 3aa |
| 2 | $NO_2$ 1b | H 2a | 1 | 98 3ba |
| 3 | $CH_3CO$ 1c | H 2a | 1 | 96 3ca |
| 4 | CN 1d | H 2a | 1 | 97 3da |
| 5 | CN 1d | CHO 2b | 1 | 98 3db |
| 6 | $CH_3O$ 1e | H 2a | 3 | 91 3ea |
| 7 | $NH_2$ 1f | H 2a | 3 | 90 3fa |
| 8 | H 1a | $CH_3$ 2c | 3 | 93 3ac |
| 9 | H 1a | $CF_3$ 2d | 3 | 88 3ad |
| 10 | H 1a | $NH_2$ 2e | 3 | 96 3ae |
| 11 | $NH_2$ 1f | $NH_2$ 2e | 4 | 88 3fe |

[a]Reaction Conditions: Pd-BOX (1 mol %), aryl iodide (1.0 mmol), alkyne (1.5 mmol), KOH (2.0 mmol), $CH_3CN$ (2 mL), $H_2O$ (2 mL), r.t.
[b]Isolated yield.

Example 7

Sonogashira Coupling of Aryl Iodides with 1,3- and 1,4-diethynyl benzenes to Yield bis(phenylethynyl)-benzene (BPEB) Derivatives Bis(phenylethynyl)-benzene (BPEB) derivatives have been commonly recognized as important components of liquid crystals for electronic displays and has been significantly applied in the production of notebook computer screens, mobile phones, flat screen monitors and LCD televisions (Beeby, A.; Findlay, K.; Low P. J.; Marder T. B.

A. J. Am. Chem. Soc. 2002, 124, 8280.s. Schwab P. F. H.; Smith, J. R.; Michl, J. Chem. Rev. 2005, 105, 1197, each incorporated herein by reference in their entirety). BPEBs are characterized by high clearing and melting point, as well as large optical anisotropy values (Tanaka T.; Sekine, C.; Ashida, T.; Ishitobi, M.; Konya, N.; Minai, M.; Fujisawa, K. Liq. Cryst. 2000, 346, 209. Liao, Y. M.; Chen, H. L.; Hsu, C. S.; Gauza, S.; Wu, S. T. Liq. Cryst. 2007, 34, 507. Li, N.; Li, Z.; Zhang, X.; Hua, R. Int. J. Mol. Sci. 2013, 14:12, 23257, each incorporated herein by reference in their entirety). The disclosed catalyst system was successfully applied to the synthesis of BPEB derivatives (Table 3). 1,3 and 1,4-Bis(phenylethynyl)-benzenes were obtained from the reactions of aryl iodides with 1,3- and 1,4-diethynyl benzenes, respectively (Table 3). Complete conversions was observed after 1-3 h (Table 3, entries 1-4), depending on the nature of the substituent and the desired cross-coupling products were isolated in excellent yields. It is noteworthy that the reactions were conducted at room temperature and the palladium catalysts showed particular air and moisture stability. This phosphine-free catalytic system represents a significant advantage, specifically when the reactions were conducted in air. Moreover, the reactions were conducted in the absence of copper, therefore, no homocoupling of the alkyne products were detected.

TABLE 3

Sonogashira coupling reaction of aryl iodides with dialkynes.
Synthesis of Bis(phenyl ethynyl)-benzene derivatives (BPEBs).

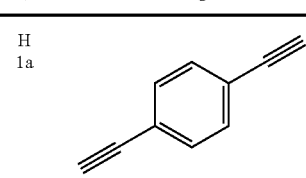

| Entry | R 1a, c | Aryl dialkyne 2f-g | Time (h) | Yield (%)[b] 4 |
|---|---|---|---|---|
| 1 | H 1a | 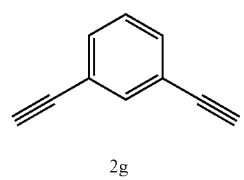 2f | 3 | 90 4af |
| 2 | H 1a | 2g | 3 | 89 4ag* |
| 3 | CH$_3$CO 1c | 2f | 1 | 97 4cf |
| 4 | CH$_3$CO 1c | 2g | 2 | 97 4cg |

[a]Reaction Conditions: Pd-BOX (1 mol %), aryl iodide (1.1 mmol), alkyne (0.5 mmol), KOH (2.0 mmol), CH$_3$CN (2 mL), H$_2$O (2 mL), r.t.
[b]Isolated yield.
*1,3-Bis(phenylethynyl) benzene (4ag): brown solid; yield 89%; $^1$H NMR (500 MHz, CDCl$_3$) δ (ppm): 7.70-7.64 (m, 1H), 7.52-7.42 (m, 6H), 7.34-7.32 (m, 7H), $^{13}$C NMR (125 MHz, CDCl$_3$) δ (ppm): 134.6, 131.6, 131.2, 128.4, 128.3, 88.5, GC-MS m/z 278 (M + 1) Anal. Calcd. for C$_{22}$H$_{14}$, (278.35): C, 94.93; H, 5.07. Found: C, 95.01.61; H 5.01.

Example 8

Sonogashira Coupling of Aryl Iodides with Alkyl Alkynes

The Sonogashira coupling reactions of aryl iodides with alkyl alkynes using palladium-phosphine catalysts have been widely studied. However, there are few reports on the copper-free and phosphine-free Sonogashira coupling of aryl iodides with alkyl alkynes. The reaction usually requires a high temperature and the product yield is low (Bakherad, M.; Keivanloo, A.; Samangooei, S.; O. Tetrahedron Lett. 2012, 53, 5773, incorporated herein by reference in its entirety).

Interestingly, the Pd-BOX complex was highly active in the cross-coupling reactions of aryl iodides with alkyl alkynes at 60° C. For instance, the coupling reactions of 4-iodoacetophenone with various alkyl alkynes gave the expected internal acetylenes in excellent yield (Table 4, entries 1 and 2). The reactions were found to be unaffected by the alkyl chain lengths, however, phenyl substituted alkyl alkyne 5c was more reactive (Table 4, entry 3). Iodobenzene also reacted efficiently with alkyl alkynes and substituted alkyl alkynes to produce the alkyl alkynes in high yields (Table 4, entries 4-6). Interesting examples were the cross-coupling reactions of trimethylsilyl acetylene (Table 4, entry 7) and triphenyl silyl acetylene (Table 4, entry 8). These reactions led predominantly to the corresponding aryl silyl acetylenes indicating that the new catalytic system containing Pd-BOX was highly effective in the coupling reactions of aryl iodides with silyl acetylenes (Ibrahim, M. B.; El Ali, B.; Malik, I.; Fettouhi, M. Tetrahedron Lett. 2016, 57, 554, incorporated herein by reference in its entirety). Similarly, a silyloxy acetylene was very reactive. However, the silyloxy group was hydrolyzed under the reaction conditions to give the corresponding alkynol (Table 4, entry 9). The cross-coupling reaction of iodobenzene with a terminal alkynol was also successful, giving the desired product in 87% yield (Table 4, entry 10).

TABLE 4

Sonogashira coupling reactions of aryl iodide with alkyl alkyne catalyzed by Pd-BOX.[a]

| Entry | R 1a, c | Alkyl alkyne 5a-j | Time (h) | Yield (%)[b] 6 |
|---|---|---|---|---|
| 1 | CH$_3$CO 1c | 5a | 3 | 95 6ca |
| 2 | CH$_3$CO 1c | 5b | 3 | 90 6cb |
| 3 | CH$_3$CO 1c | 5c | 2 | 98 6cc |
| 4 | H 1a | 5d | 4 | 95 6ad |
| 5 | H 1a | 5e | 4 | 90 6ae |
| 6 | H 1a | 5f | 4 | 92 6af |
| 7 | H 1a | 5g | 4 | 93 6ag |
| 8 | H 1a | 5h | 4 | 95 6ah* |
| 9[c] | H 1a | 5i | 4 | 90 6ai |
| 10 | H 1a | 5j | 4 | 87 6aj |

[a]Reaction Conditions: Pd-BOX (1 mol %), aryl iodide (1.0 mmol), alkyl alkyne (1.5 mmol), KOH (2.0 mmol), CH$_3$CN (2 mL), H$_2$O (2 mL), 60° C.
[b]Isolated yield.
[c]The hydrolyzed product was obtained.
*6-phenylhex-5-ynenitrile (6ah): yellow oil; yield 90%; $^1$H NMR (500 MHz, CDCl$_3$) δ (ppm): 7.34-7.32 (m, 2H), 7.24-7.22 (m, 3H), 2.53 (t, J = 6.7 Hz, 2H), 2.49 (t, J = 7.3 Hz, 2H), 1.89 (m, 2H); $^{13}$C NMR (125 MHz, CDCl$_3$) δ (ppm): 131.5, 128.2, 127.9, 123.1, 119.1, 86.8, 82.3, 24.6, 18.5, 16.1, GC-MS m/z 169 (M + 1) Anal. Calcd. for C$_{12}$H$_{11}$N (169.08): C, 85.17; H, 6.55; N, 8.28. Found: C, 85.21; H, 6.62; N, 8.73.

Example 9

Sonogashira Coupling Reaction of Aryl Iodide with octa-1,7-diyne

Interestingly, the terminal dialkyl alkyne, octa-1,7-diyne, coupled smoothly with 4-iodoacetophenone to afford the corresponding internal dialkynyl ketone in excellent yield.

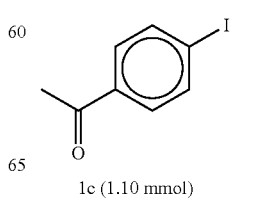

1c (1.10 mmol)

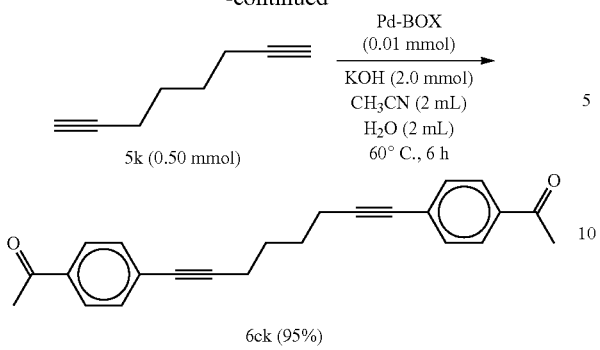

6ck (95%)

Example 10

Sonogashira Coupling Reaction of Diiodobenzene with Aryl and Alkyl Alkynes

The Sonogashira coupling reaction of diiodobenzene with aryl and alkyl alkynes gave new internal alkynes in excellent yields (Table 5). The reactions of 1,4-diiodobenzene with phenylacetylene or 4-ethynyl aniline (Table 5, entries 1 and 2) successfully yielded the corresponding bis(phenylethynyl)-benzene derivatives. Similarly, the reaction of 1,4-diiodobenzne with various alkyl alkynes gave the corresponding symmetrically disubstituted alkynyl benzenes in excellent yields (Table 5, entries 3-7). Alkynols and alkyndiols represent important building blocks for the synthesis of a wide variety of industrially and pharmaceutically important heterocycles (Alcaide, B.; Almendros, P.; Alonso, J. M. Org. Biomol. Chem. 2011, 9, 4405, incorporated herein by reference in its entirety). Representative dialkyndiols, 4,4'-benzene-1,4-diylbisbut-3-yn-1-ol (Table 5, entry 6) and 1,1'-benzene-1,4-diylbis-(3,4-dimethylpent-1-yn-3-ol) (Table 5, entry 7), were successfully synthesized from the coupling of 1,4-diiodobenzene with 1-trimethylsiloxy-3-butyne and 3,5-dimethylhex-1-yn-3-ol, respectively.

TABLE 5

Sonogashira coupling reaction of 1,4-diiodobenzene with aryl and alkyl alkynes.[a]

| Entry | Alkyne 2 | Yield (%)[b] 7 |
|---|---|---|
| 1 | 2a (phenylacetylene) | 95 7ga |
| 2 | 4-ethynylaniline (2e) | 96 7ge |
| 3 | 5f (1-pentyne) | 96 7gf |
| 4 | 5h (CN-substituted alkyne) | 95 7gh* |
| 5 | 5g (Cl-substituted alkyne) | 96 7gg# |
| 6 | 5l (OSi(CH3)3 alkyne) | 90 7gl |
| 7 | 5o (OH alkyne) | 93 7go† |

[a]Reaction Conditions: Pd-BOX (1 mol %), 1,4-diiodobenzene (0.5 mmol), alkyne (1.5 mmol), KOH (2.0 mmol), CH₃CN (2 mL), H₂O (2 mL), 60° C., 12 h.
[b]Isolated yield.
*1,4-Bis(5-chloropent-1-yn-1-yl)benzene (7gh): yellow oil, yield 96%; $^1$NMR (500 MHz, CDCl₃) δ (ppm): 7.24 (s, 4H), 4.0 (t, J = 6.4 Hz, 4H), 2.54 (t, J = 6.7 Hz, 4H), 1.98 (m, 4H); $^{13}$C NMR (125 MHz, CDCl₃) δ (ppm): 131.3, 122.9, 89.7, 81.2, 43.7, 31.3, 16.9; IR (CH₂Cl₂, v cm⁻¹) 2947, 2230, 1915, 1706, 1501, 1437, 1283, 1064; GC-MS m/z 279 (M+) Anal. Calcd. for C₁₆H₁₆Cl₂ (279.21): C, 68.83; H, 5.78. Found: C, 68.51; H, 5.43.
6,6'-Benzene-1,4-diylbishex-5-ynenitrile (7gg): yellow oil, yield 95%; $^1$H NMR (500 MHz, CDCl₃) δ (ppm): 7.29 (s, 4H), 2.59 (t, J = 6.7 Hz, 4H), 2.53 (t, J = 7.3 Hz, 4H), 1.94 (m, 4H); $^{13}$C NMR (125 MHz, CDCl₃) δ (ppm): 132.2, 123.5, 119.8, 89.4, 82.8, 25.2, 19.3, 16.9; IR (KBr, v cm⁻¹) 2953, 2246, 1919, 1672, 1505, 1446, 1296, 1215, 1056, 838; GC-MS m/z 260 (M+). Anal. Calcd. for C₁₈H₁₆N₂ (260.13): C, 83.04; H, 6.19; N, 10.76. Found: C, 83.24; H, 6.23; N, 10.92.
†1,4-Bis(3,5-dimethyl-1-hex-1-yn-3-ol) benzene (7go): yellow viscous oil, yield 93%; $^1$H NMR (500 MHz, CDCl₃) δ (ppm): 7.31 (s, 4H), 1.98 (m, 2H), 1.67 (d, J = 6.2 Hz, 4H), 1.55 (s, 6H); 1.03 (d, J = 4.6 Hz, 12H), $^{13}$C NMR (125 MHz, CDCl₃) δ (ppm): 131.4, 122.6, 95.0, 83.1, 68.5, 51.9, 30.9, 25.2, 24.2; IR (CH₂Cl₂, v cm⁻¹) 3373, 2953, 2225, 1910, 1658, 1457, 1367, 1153, 926, 834; GC-MS m/z 326 (M+) Anal. Calcd. for C₂₂H₃₀O₂, (326.22): C, 80.94; H, 9.26. Found: C, 80.61; H, 9.33.

The invention claimed is:

1. A palladium(II) complex, which is:

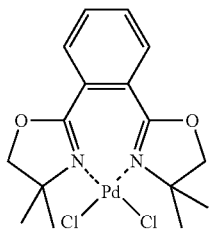

2. A method for preparing a compound of formula Ar—C≡C—R¹, the method comprising:
reacting a compound of formula ArY with a compound of formula HC≡CR¹ in the presence of a solvent, a base, and a palladium(II) complex of formula (I):

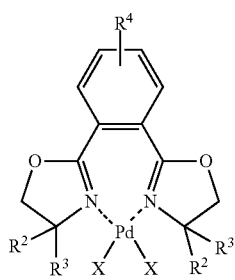

(I)

wherein the solvent comprises 5-95% by volume of water and 5-95% by volume of acetonitrile, based on a total volume of the solvent,
thereby yielding the compound of formula Ar—C≡C—R¹, wherein:
Ar is an optionally substituted aryl group,
Y is I, Br, Cl, OTf, or OTs,
R¹ is an optionally substituted alkyl group, or an optionally substituted aryl group,
R², R³, and R⁴ are each independently a hydrogen atom, an optionally substituted alkyl group, or an optionally substituted aryl group, and
X is I, Br, Cl, OTf, or OAc.

3. The method of claim 2, which is performed in air, in the absence of a phosphine, and in the absence of a copper(I) complex.

4. The method of claim 2, wherein the compound of formula ArY is an aryl monohalide or an aryl dihalide.

5. The method of claim 4, wherein the compound of formula ArY is at least one selected from the group consisting of iodobenzene, 4-iodoaniline, 4-iodoacetophenone, 4-iodobenzonitrile, 4-iodoanisole, 1-iodo-4-nitrobenzene, and 1,4-diiodobenzene.

6. The method of claim 2, wherein the compound of formula HC≡CR¹ is a monoalkyne or a dialkyne.

7. The method of claim 6, wherein the compound of formula HC≡CR¹ is at least one monoalkyne selected from the group consisting of phenylacetylene, 4-ethynylaniline, 4-ethynylbenzaldehyde, 4-ethynyholuene, 4-ethynyl-α,α,α-trifluorotoluene, 1-hexyne, 1-octyne, 1-decyne, 1-dodecyne, 4-phenyl-1-butyne, 5-phenyl-1-pentyne, 5-chloro-1-pentyne, 5-hexynenitrile, 3,3-dimethyl-1-butyne, ethynyltrimethylsilane, (triphenylsilyl)acetylene, 4-(tert-butyldimethylsilyloxy)-1-butyne, 3,4-dimethyl-1-pentyn-3-ol, 1-hexyne, and 3,5-dimethyl-1-hexyn-3-ol, or at least one dialkyne selected from the group consisting of 1,4-diethynylbenzene, 1,3-diethynylbenzene, and 1,7-octadiyne.

8. The method of claim 2, wherein a molar ratio of the compound of formula ArY to the compound of formula HC≡CR¹ ranges from 2:1 to 2:15.

9. The method of claim 2, wherein a molar ratio of the base to the compound of formula ArY ranges from 1:1 to 8:1.

10. The method of claim 9, wherein the molar ratio of the base to the compound of formula ArY ranges from 2:1 to 4:1.

11. The method of claim 2, wherein an amount of the palladium(II) complex ranges from 0.1-10 mol % relative to a number of moles of the compound of formula ArY.

12. The method of claim 11, wherein the amount of the palladium(II) complex ranges from 1-5 mol % relative to the number of moles of the compound of formula ArY.

13. The method of claim 2, wherein the solvent consists of 50% by volume of water and 50% by volume of acetonitrile, based on the total volume of the solvent.

14. The method of claim 2, wherein the base is at least one selected from the group consisting of an alkali metal hydroxide, an alkali metal carbonate, and an amine.

15. The method of claim 2, wherein the reacting is performed at a temperature ranging from 18-60° C.

16. The method of claim 2, wherein the palladium(II) complex is

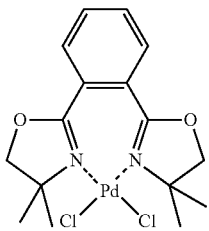

17. A method for preparing a compound of formula Ar—C≡C—R¹, the method comprising:
reacting a compound of formula ArY with a compound of formula HC≡CR¹ in the presence of a solvent, a base, and the palladium(II) complex of claim 3, thereby yielding the compound of formula Ar—C≡C—R¹, wherein:
Ar is an optionally substituted aryl group,
Y is I, Br, Cl, OTf, or OTs, and
R¹ is an optionally substituted alkyl group, or an optionally substituted aryl group.

18. The method of claim 17, wherein the solvent comprises acetonitrile.

* * * * *